US005843009A

United States Patent [19]

Stojanović

[11] Patent Number: 5,843,009

[45] Date of Patent: *Dec. 1, 1998

[54] THERAPEUTIC TREATMENT DEVICE

[76] Inventor: Branislav Stojanović, D. Stojanovića 6, 21000 Novi Sad, Yugoslavia

[ * ] Notice: The term of this patent shall not extend beyond the expiration date of Pat. No. 5,498,233.

[21] Appl. No.: 605,260

[22] Filed: Dec. 26, 1995

Related U.S. Application Data

[63] Continuation of Ser. No. 322,060, Oct. 12, 1994, Pat. No. 5,498,233, which is a continuation of Ser. No. 855,772, Mar. 23, 1992, abandoned.

[30] Foreign Application Priority Data

Mar. 22, 1991 [YU] Yugoslavia ................................ 505/91

[51] Int. Cl.$^6$ ........................................................ A61F 5/02

[52] U.S. Cl. ................................ 602/19; 602/18; 128/845

[58] Field of Search .................................... 606/201, 204, 606/240; 602/13, 18, 19; 600/9, 12, 13, 14, 15; 482/105; 2/92; 128/845, 781, 907

[56] References Cited

U.S. PATENT DOCUMENTS

| | | | |
|---|---|---|---|
| 2,447,698 | 10/1948 | Haberer . | |
| 3,360,731 | 12/1967 | Tigges . | |
| 4,230,099 | 10/1980 | Richardson . | |
| 4,411,258 | 10/1983 | Pujals, Jr. | 606/204 |
| 4,716,898 | 1/1988 | Chaure et al. | 602/19 |
| 4,760,842 | 8/1988 | Holmes . | |
| 4,953,857 | 9/1990 | Lemire | 482/105 |
| 5,007,633 | 4/1991 | Lamire . | |
| 5,035,017 | 7/1991 | Komuro . | |
| 5,048,509 | 9/1991 | Grundei et al. . | |
| 5,120,288 | 6/1992 | Sinaki . | |
| 5,140,995 | 8/1992 | Uhl . | |
| 5,158,073 | 10/1992 | Bukowski . | |
| 5,267,947 | 12/1993 | James et al. . | |
| 5,290,307 | 3/1994 | Choy . | |
| 5,312,350 | 5/1994 | Jacobs . | |
| 5,328,447 | 7/1994 | Kapounek et al. . | |
| 5,437,614 | 8/1995 | Grim . | |

FOREIGN PATENT DOCUMENTS

| | | | |
|---|---|---|---|
| 2187284 | 10/1987 | France . | |
| 120697 | 5/1901 | Germany . | |
| 2128410 | 12/1972 | Germany | 602/19 |
| 2334500 | 1/1975 | Germany . | |
| 2506647 | 10/1976 | Germany . | |
| 3525521 A1 | 1/1987 | Germany . | |
| 1120-997-A | 10/1984 | U.S.S.R. . | |
| 2193429 | 2/1988 | United Kingdom . | |
| WO 86/05091 | 9/1986 | WIPO . | |

*Primary Examiner*—Jeanne M. Clark
*Attorney, Agent, or Firm*—Baker & McKenzie

[57] ABSTRACT

A device for therapeutic treatment of a body including a segment comprising spatially separated bulges. A plurality of segments may optionally be linked together so as to increase the area of the body upon which the device is placed.

23 Claims, 3 Drawing Sheets

THERAPEUTIC TREATMENT DEVICE

This is a continuation of application Ser. No. 08/322,060, filed on Oct. 12, 1994, and issued on Mar. 12, 1996 as U.S. Pat. No. 5,498,233, which is a continuation of application Ser. No. 07/855,772, filed on Mar. 23, 1992, now abandoned.

BACKGROUND OF THE INVENTION

1. Field of the Invention

The invention relates to a device applied as a therapeutic helping device.

2. Brief Description of the Background of the Invention

A technical problem solved by the invention is a construction of a device to make possible the placement of segments on the body by using segments with protruding elements, bulges, recesses.

SUMMARY OF THE INVENTION

Purpose of the Invention

It is an object of the present invention to provide a device for therapeutic treatment of a body.

It is another object of the present invention to provide a local treatment of the cervical or lumbar part of the spine.

It is yet a further object of the present invention to provide an optimal system for therapeutic treatment of the whole spine.

These and other objects and advantages of the present invention will become evident from the description which follows.

Brief Description of the Invention

A device for therapeutic treatment, according to this invention, consists of one or more segments, each of them having numerous protruding elements, bulges and grooves. The protruding elements exhibit on their two ends numerous transversal carved notches and grooves and two grooves on the upper side between every third pair of protruding elements. Segments can be connected with other segments in a row, using corresponding pins and holes. The number of segments linked together can vary depending upon the extent, i.e. the length of spine, i.e. the area surrounding the spine which needs treatment.

The device consists of segments which can be used individually for local treatment of the cervical or lumbar part of the spine, or in a row, when it represents an optimal system for treatment of the whole spine.

The invention device may be activated in its original embodiment without the casing by placement onto a lying body, or by fastening the invention device within the casing with belts to a body of a person when the person is in an upright, sitting, lying, or walking position.

The novel features which are considered as characteristic for the invention are set forth in the appended claims. The invention itself, however, both, as to, its construction and its method of operation, together with additional objects and advantages thereof, will be best understood from the following description of specific embodiments when read in connection with the accompanying drawings.

BRIEF DESCRIPTION OF THE DRAWINGS

In the accompanying drawings, in which are shown several of the various possible embodiments of the present invention.

DESCRIPTION OF INVENTION AND PREFERRED EMBODIMENT

Figure 1:
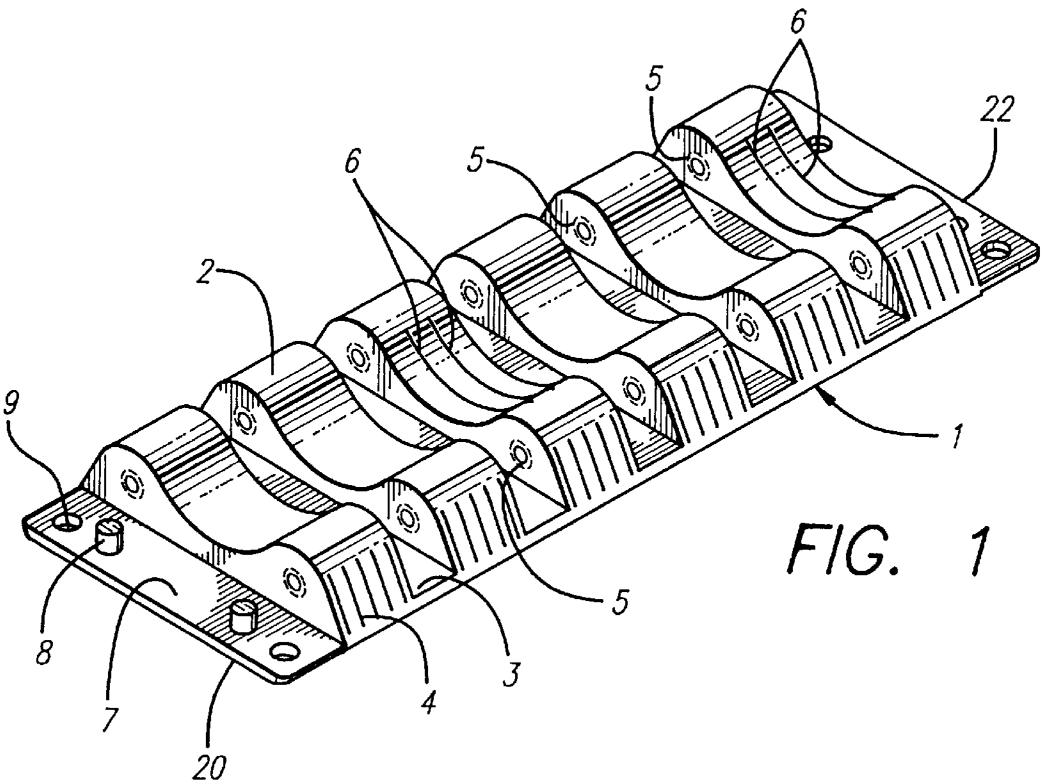
FIG. 1 illustrates a perspective top view onto a device for energetic activation of a spine system.
Figure 2:
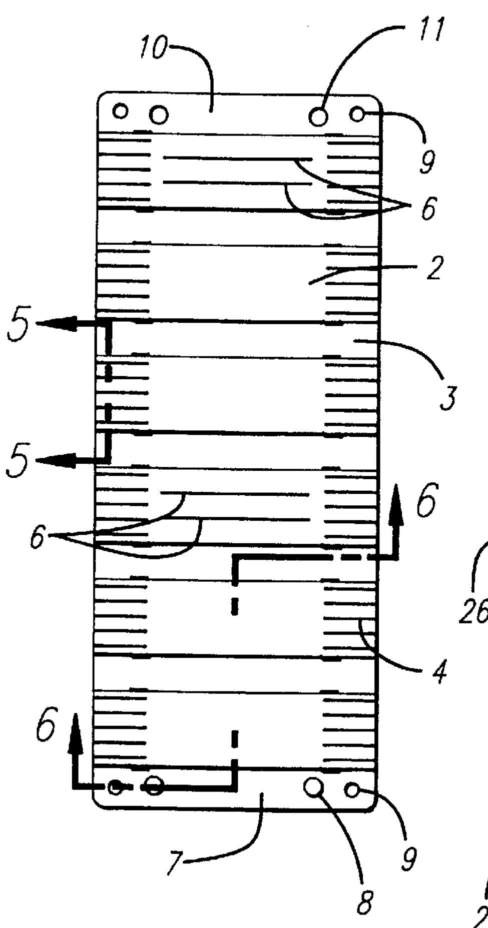
FIG. 2 illustrates a planar view of the invention device.
Figure 3:
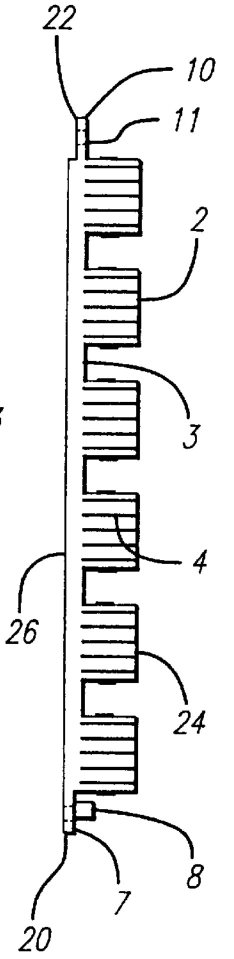
FIG. 3 illustrates a side view of the invention device.
Figure 5:
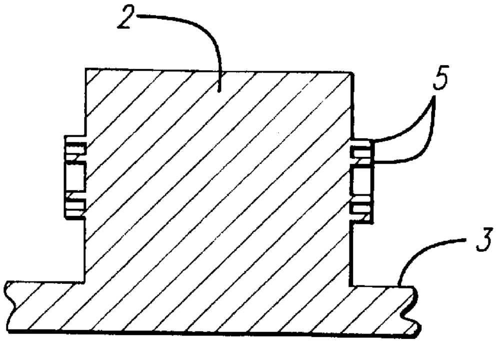
FIG. 5 illustrates a cross-sectional view of the invention device along section line B—B of FIG. 2.
Figure 6:
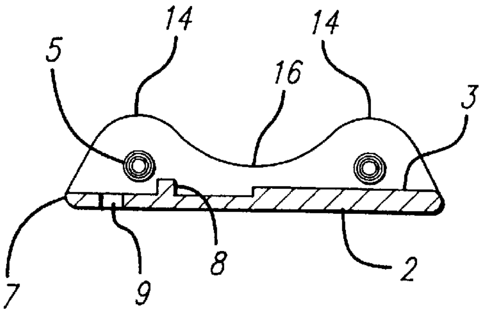
FIG. 6 illustrates a cross-sectional view of the invention device along section line A—A of FIG. 2.

The invention device for therapeutic treatment of a spine consists of one or more segments 1. As illustrated in FIG. 1, a segment 1 exhibits a plurality of protruding elements 2 and recessed surfaces 3 disposed on a first face 24 (FIG. 3) of the segment 1. The two ends of each protruding element 2 exhibit on their outer end surface a plurality of carved notches and grooves (engravings) 4. The protruding element 2 exhibits an undulating shape, where a peak 14 is formed at each end of the protruding element 2, and where a valley 16 is formed between said two peaks 14 (FIG. 6). As illustrated in FIG. 2, two grooves 6 are disposed in the valley 16 of each third protruding element 2. A cylindrical outlet projection 5, illustrated in FIG. 5, is disposed concentrically in the curve of each peak 14 on the longitudinal faces of the protruding element 2. As illustrated in FIGS. 2 and 3, the first end 20 of the segment 1 forms a first connection strip 7. The connection strip 7 is provided with two cylindrical pins 8 and two holes 9. The second end 22 of the segment 1, disposed opposite to the first end 20, forms a second connection strip 10. The second connection strip 10 is provided with two pairs of holes 9 and 11 When linking two or more segments 1 to each other to form a row 28 of segments, the cylindrical pin 8 of the first connection strip 7 of one segment 1 is in each case placed into the hole 11 of the second connection strip 10 of a following segment 1.

Figure 4:
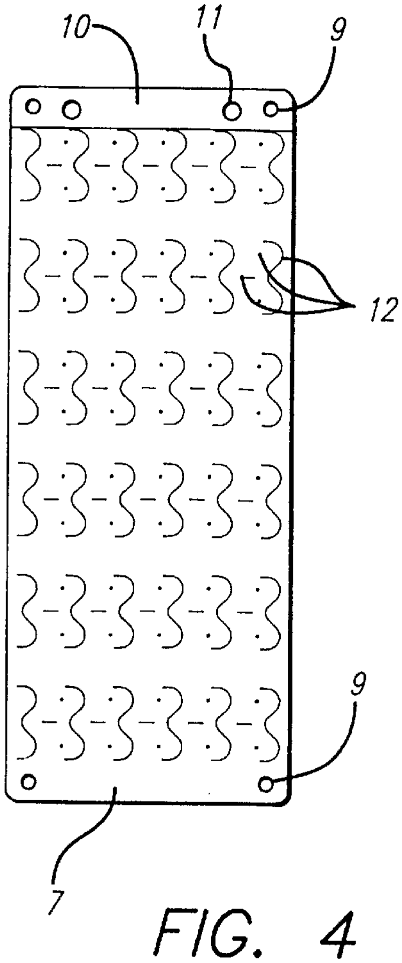
FIG. 4 illustrates a bottom of the invention device.

As illustrated in FIG. 4, the segment 1 exhibits a plurality of projections, notches, and outlets 12, shaped as lines and dots, on the second face 26.

The row 28 of segments 1 can be used for treatment of the whole spine. A desired number of segments 1, forming the row 28, are placed along the spine of a person in a horizontal position, wherein the peaks 14 of the protrusions 2 of the segments 1 are placed on either side of the spine, thereby contouring to the shape of the vertebral column.

Figure 8:
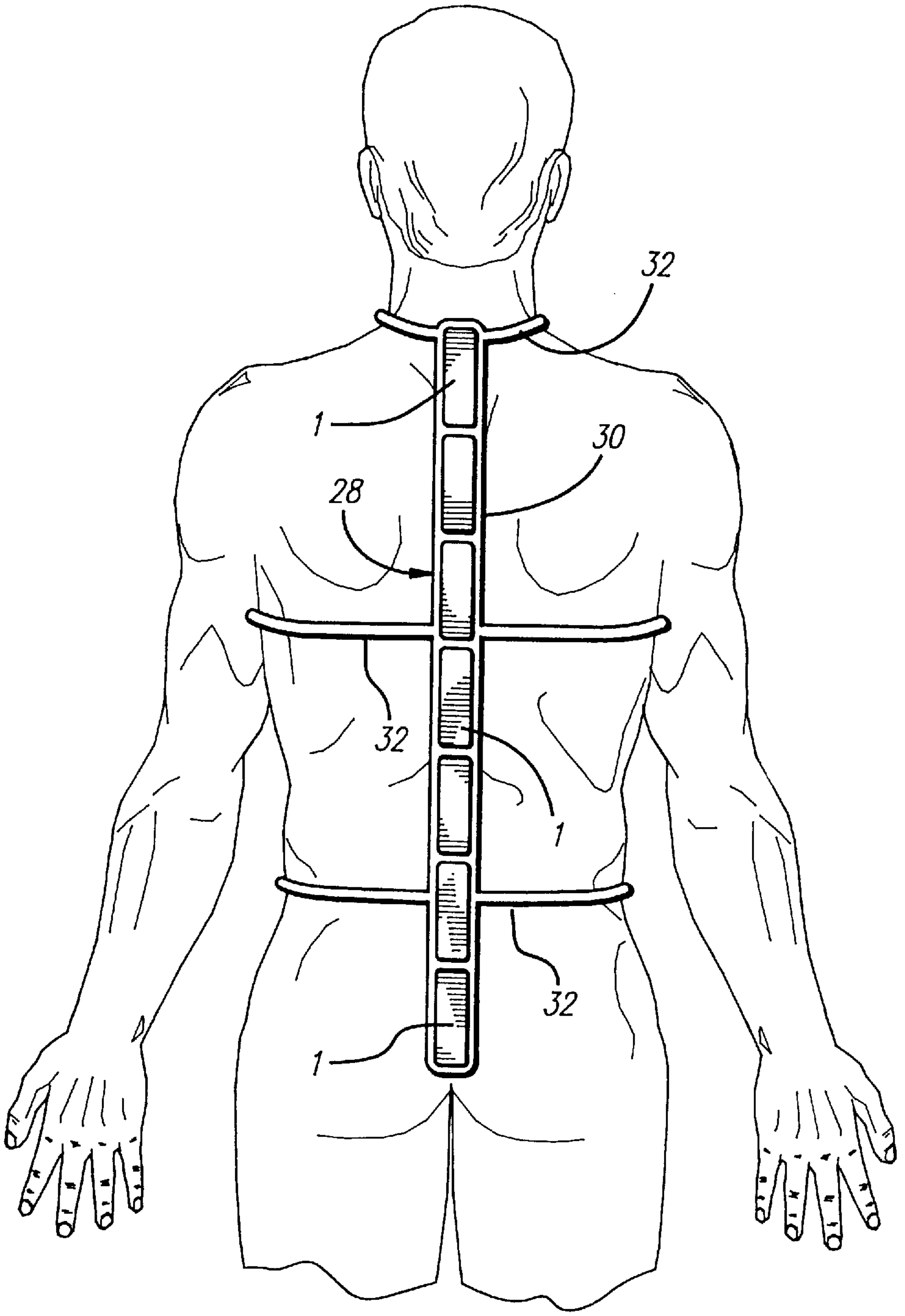
FIG. 8 illustrates an exemplified embodiment of a series of segments disposed in a casing and applied against the length of the spine.

As illustrated in FIG. 8, the row 28 of segments 1 can be placed into a casing 30. The casing 30 includes fastening straps 32 placed at a distance from each other on the, two lateral sides of the casing 30. The casing 30, including the row 28 of segments 1, can be placed against the spinal column of a person and fastened to the body of the person by the fastening straps 32, thereby allowing the person to wear the invention device while in an upright position, i.e. the invention device can be worn while the person, wearing the device, can pursue any desired activity. While a person is wearing the invention device, the spine of the person in question is treated correctly.

Figure 7:
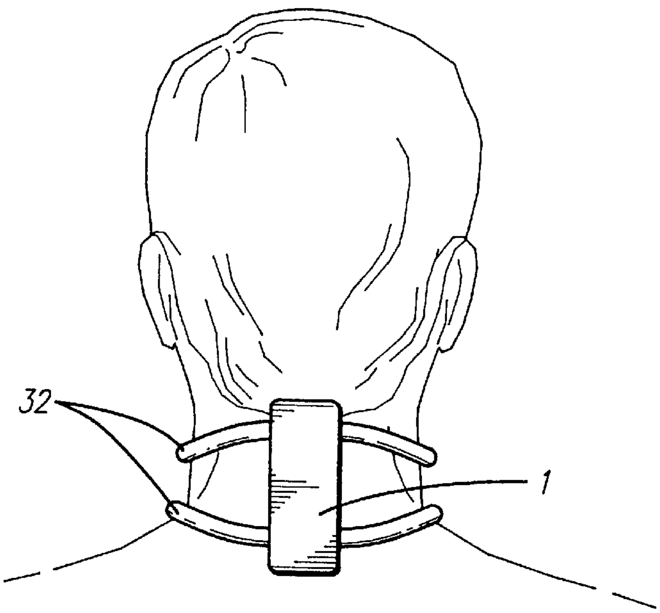
FIG. 7 illustrates an exemplified embodiment of one segment of the invention device placed against the cervical section of the spine.

If it is not necessary to treat the entire length of the spine, it is possible to place the desired number of segments 1 into a casing 30, having a length corresponding to the number of segments 1, and to fasten said casing 30 including the desired number of segments 1, covering the desired part of the spine to be treated, with the fastening straps 32 to the body of the person. An exemplified embodiment of the employment of one segment 1 in a casing 30 is shown in FIG. 7.

It will be understood that each of the elements described above, or two or more together, may also find a useful application in other types of arrangements for therapeutic treatments differing from the types described above.

While the invention has been illustrated and described as embodied in the context of a device for energetic activation of a spine system, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A therapeutic device for being positioned on a user's body comprising:

at least one segment wherein each segment comprises:

a discrete mounting structure elongated in a longitudinal direction and including a mounting surface;

a plurality of elements permanently attached to and protruding from the mounting structure, wherein:

each of the elements has a top face opposite the mounting surface and said top face has an undulating shape with a plurality of peaks;

each peak has a summit and downwardly sloping sides; and the elements are longitudinally spaced apart from one another on the mounting surface.

2. The device of claim 1 wherein:

each of the elements is integrally formed with the mounting structure forming a unitary one-piece structure including the elements and the mounting structure;

each of the plurality of elements includes two peaks wherein the two peaks are laterally spaced from one another and are integrally formed with the respective element.

3. The device of claim 2 wherein:

each of the plurality of elements includes a curved recess between the spatially separated two peaks on the element;

the two peaks on each of the plurality of elements protrude away from the mounting surface in a convex fashion;

the curved recess between the peaks of each of the plurality of elements is a concave recess; and the peaks and recess of each contact element are integrally formed with one another.

4. The device of claim 1 wherein:

each of the elements is integrally formed with the mounting structure forming a unitary one-piece structure including the elements and the mounting structure;

the plurality of peaks on each of said plurality of elements are laterally spaced from each other and are integrally formed with the respective element.

5. The device of claim 4 wherein each of the plurality of peaks on any one of said plurality of elements are arranged in a row wherein each of the peaks is laterally spaced apart from at least one other peak on the respective element.

6. The device of claim 4 wherein:

each of the plurality of elements includes at least one curved recess wherein one of said curved recess is between each of the respective spatially separated peaks on the respective element;

each of the peaks on each of the plurality of elements protrude away from the mounting surface in a convex fashion;

each curved recess extends towards the mounting surface in a concave fashion.

7. The device of claim 1 further comprising a plurality of apertures defined in the mounting surface, and a fastener inserted through at least one said aperture.

8. The device of claim 7 wherein the fastener includes a flexible elongated member configured to align the device such that the top faces of the contact elements apply pressure to the body at their respective points of contact with the body.

9. The device of claim 1 wherein the mounting structure has a proximal side including the mounting surface and a distal side opposite the proximal side, the distal side comprising a plurality of notches and projections.

10. The device of claim 1 further comprising a means for fastening the device to a desired portion of the body of a person.

11. The device of claim 1 wherein each of the plurality of elements is integrally formed with the mounting structure forming a unitary one-piece structure including the elements and the mounting structure.

12. The device of claim 1 wherein the plurality of peaks on any one of said plurality of elements are arranged in at least one row of peaks wherein each row of peaks includes at least two peaks, each peak being laterally spaced apart from any adjacent peak in the respective row.

13. A therapeutic device for being positioned on a user's body comprising:

at least one segment wherein each segment comprises:

a discrete mounting structure elongated in a longitudinal direction and including a mounting surface;

a plurality of elements integrally formed with the mounting structure forming a unitary one-piece structure including the elements and the mounting structure, wherein:

each of the elements has a top face opposite the mounting surface and said top face has an undulating shape with a plurality of peaks;

each peak has a summit and downwardly sloping sides; and the elements are longitudinally spaced apart from one another on the mounting surface.

14. The device of claim 13 wherein the top face of each of the elements is integrally formed with the element and each element has a single top face.

15. The device of claim 13 further comprising a means for fastening the device to a desired portion of the body of a person.

16. The device of claim 13 wherein the plurality of peaks on any one of said plurality of elements are arranged in at least one row of peaks wherein each row of peaks includes at least two peaks, each peak being laterally spaced apart from any adjacent peak in the respective row.

17. The device of claim 13 wherein the mounting structure has a proximal side including the mounting surface and a distal side opposite the proximal side, the distal side comprising a plurality of projections.

18. A therapeutic device for being positioned on a user's body comprising:

at least one segment wherein each segment comprises:

a discrete mounting structure elongated in a longitudinal direction and including a mounting surface;

a plurality of elements fixedly attached to and protruding from the mounting structure, wherein:

each of the elements has a top face opposite the mounting surface and said top face has an undulating shape with a plurality of peaks;

each peak has a summit and downwardly sloping sides; and the elements are longitudinally spaced apart from one another on the mounting surface; and wherein the plurality of peaks on any one of said plurality of elements are arranged in at least one row of peaks wherein each row of peaks includes at least two peaks, each peak being laterally spaced apart from any adjacent peak in the respective row.

19. The device of claim 18 wherein the peaks in each respective row of each respective element are spaced apart from each other by generally same distance and the peaks in adjacent elements are longitudinally aligned, forming generally linear columns.

20. A therapeutic device for being positioned on a user's body comprising:

at least one segment wherein each segment comprises:

a discrete mounting structure elongated in a longitudinal direction and including a mounting surface;

a plurality of elements fixedly attached to and protruding from the mounting structure, wherein:

each of the elements has a top face opposite the mounting surface and said top face has an undulating shape with a plurality of peaks;

each peak has a summit and downwardly sloping sides; and the elements are longitudinally spaced apart from one another on the mounting surface; and the device further comprising a means for fastening the device to a desired portion of the body of a person wherein the means for fastening secures the device to the body such that the device stays secured while the person is in an upright position.

21. A therapeutic device for being positioned on a user's body comprising:

a plurality of linkable segments wherein each linkable segment comprises:

a discrete mounting structure elongated in a longitudinal direction and including a mounting surface;

a plurality of elements fixedly attached to and protruding from the mounting structure wherein:

each of the elements has a top face opposite the mounting surface and said top face has an undulating shape with a plurality of peaks, each peak having a summit and downwardly sloping sides; and the elements are longitudinally spaced apart from one another on the mounting surface.

22. The therapeutic device of claim 21 further comprising:

a linking means for linking the plurality of segments in a row, said linking means including at least one aperture defined in at least one of the segments;

at least two spatially separated peaks on each element; and a fastener attached to at least one segment for fastening the row of segments to the user's body along a spine of the user's body such that the spatially separated peaks on each element engage the body on opposite sides of the spine.

23. A therapeutic device for being positioned on a user's body comprising:

at least one segment wherein each segment comprises:

a discrete mounting structure elongated in a longitudinal direction and including a mounting surface;

a plurality of elements integral with the mounting structure forming a unitary one-piece structure and the elements protruding from the mounting surface wherein:

each of the elements has a top face opposite the mounting surface and said top face has an undulating shape with a plurality of peaks;

the elements are longitudinally spaced apart from one another on the mounting surface wherein each element is adjacent to at least one other element;

the peaks on each of the respective elements are arranged in at least one row;

the peaks in each row are spatially separated from one another by a fixed distance; and the peaks in each of said rows are longitudinally aligned wherein at least two columns are formed by the peaks in adjacent elements.

* * * * *